(12) United States Patent
Gunaratnam et al.

(10) Patent No.: US 8,567,402 B2
(45) Date of Patent: *Oct. 29, 2013

(54) MASK PORTS

(75) Inventors: Michael K. Gunaratnam, Marsfield (AU); Amal Amarasinghe, West Pennant Hills (AU)

(73) Assignee: ResMed Limited, Bella Vista (AU)

( * ) Notice: Subject to any disclaimer, the term of this patent is extended or adjusted under 35 U.S.C. 154(b) by 342 days.

This patent is subject to a terminal disclaimer.

(21) Appl. No.: 12/656,218

(22) Filed: Jan. 21, 2010

(65) Prior Publication Data

US 2010/0122701 A1  May 20, 2010

Related U.S. Application Data

(63) Continuation of application No. 10/162,234, filed on Jun. 5, 2002, now Pat. No. 7,669,599, which is a continuation of application No. 09/504,234, filed on Feb. 15, 2000, now Pat. No. 6,439,230, which is a continuation-in-part of application No. 29/115,618, filed on Dec. 16, 1999, now Pat. No. Des. 443,355.

(30) Foreign Application Priority Data

Jun. 18, 1999 (AU) ........................................ 1916/99
Jun. 18, 1999 (AU) ........................................ PQ 1040

(51) Int. Cl.
*A62B 18/10* (2006.01)
*A62B 18/08* (2006.01)
*A62B 18/02* (2006.01)
*A61M 16/00* (2006.01)
*A61M 15/00* (2006.01)
*A61M 15/08* (2006.01)
*F16K 31/02* (2006.01)

(52) U.S. Cl.
USPC ............ 128/205.25; 128/206.21; 128/204.18; 128/206.12; 128/206.27; 128/206.28; 128/207.18; 128/204.12; 128/204.13; 128/204.23; 128/207.12; 128/207.13

(58) Field of Classification Search
USPC ............ 128/206.21, 204.18, 206.12, 205.25, 128/206.27, 206.28, 207.18, 204.12, 128/204.13, 204.23, 207.12, 207.13
See application file for complete search history.

(56) References Cited

U.S. PATENT DOCUMENTS

| 718,785 A | 1/1903 | McNary |
|---|---|---|
| 4,231,363 A | 11/1980 | Grimes |

(Continued)

FOREIGN PATENT DOCUMENTS

| AU | 200014935 A1 | 2/2000 |
|---|---|---|
| DE | 29700093 | 3/1997 |

(Continued)

OTHER PUBLICATIONS

Photograph copies of Tejon Mask, 5 pages, first sold May 1999.

(Continued)

*Primary Examiner* — Patricia Bianco
*Assistant Examiner* — Nihir Patel
(74) *Attorney, Agent, or Firm* — Nixon & Vanderhye, PC

(57) ABSTRACT

Mask ports 180 for attaching supplemental oxygen tubes 510 or measurement devices to a respiratory mask are downwardly directed and recessed into the base 110 of the mask frame 100. The ports may comprise a pair of downwardly extending tubular spigots 185 each housed in a respective recess 190 in the base 110, with a shallow bridging recess 290 therebetween for receiving a bridging piece 300 of a closure cap 280.

28 Claims, 4 Drawing Sheets

(56) References Cited

U.S. PATENT DOCUMENTS

| | | | |
|---|---|---|---|
| 4,782,832 A | 11/1988 | Trimble et al. | |
| 4,807,617 A | 2/1989 | Nesti | |
| 4,944,310 A | 7/1990 | Sullivan | |
| 5,143,061 A * | 9/1992 | Kaimer | 128/206.24 |
| 5,233,978 A | 8/1993 | Callaway et al. | |
| 5,311,862 A | 5/1994 | Blasdell et al. | |
| 5,375,593 A | 12/1994 | Press | |
| 5,429,683 A | 7/1995 | Le Mitouard | |
| 5,474,060 A | 12/1995 | Evans | |
| 5,474,063 A | 12/1995 | Riendeau | |
| 5,538,000 A | 7/1996 | Rudolph | |
| 5,724,965 A | 3/1998 | Handke et al. | |
| 5,918,598 A * | 7/1999 | Belfer et al. | 128/206.25 |
| 5,975,077 A | 11/1999 | Hofstetter et al. | |
| 6,196,223 B1 | 3/2001 | Belfer et al. | |
| D443,355 S | 6/2001 | Gunaratnam et al. | |
| 6,354,293 B1 | 3/2002 | Madison | |
| 6,439,230 B1 * | 8/2002 | Gunaratnam et al. | 128/206.21 |
| 6,478,026 B1 | 11/2002 | Wood | |
| 7,669,599 B2 * | 3/2010 | Gunaratnam et al. | 128/205.25 |
| 2002/0157672 A1 | 10/2002 | Gunaratnam et al. | |

FOREIGN PATENT DOCUMENTS

| | | |
|---|---|---|
| FR | 2 766 723 | 2/1999 |
| FR | 02766723 | 2/1999 |
| GB | 649689 | 1/1951 |
| JP | 6-508272 | 9/1994 |
| JP | 8-57054 | 3/1996 |
| JP | 10-295817 | 11/1998 |

OTHER PUBLICATIONS

English Translation of Office Action from copending Japanese Application No. 2001-504442, mailed Dec. 8, 2009, 2 pages.

English Translation of Notice of Reason(s) for Rejection for corresponding Japanese Application No. 2010-131362, mailed Jul. 17, 2012, 2 pages.

* cited by examiner

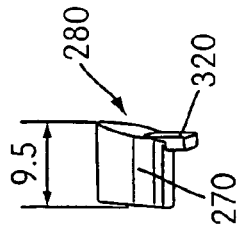
FIG. 4b
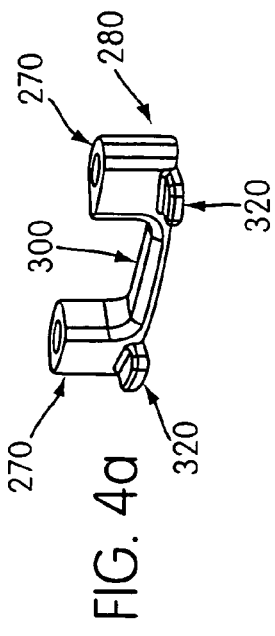
FIG. 4a
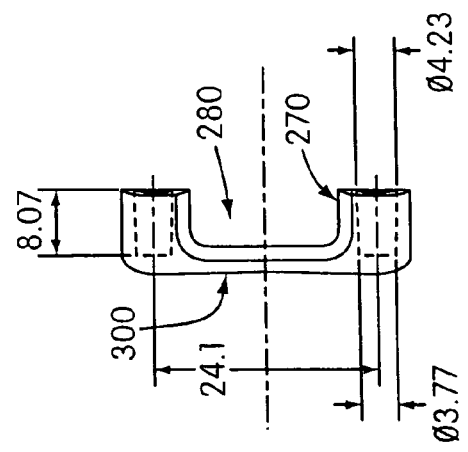
FIG. 4f
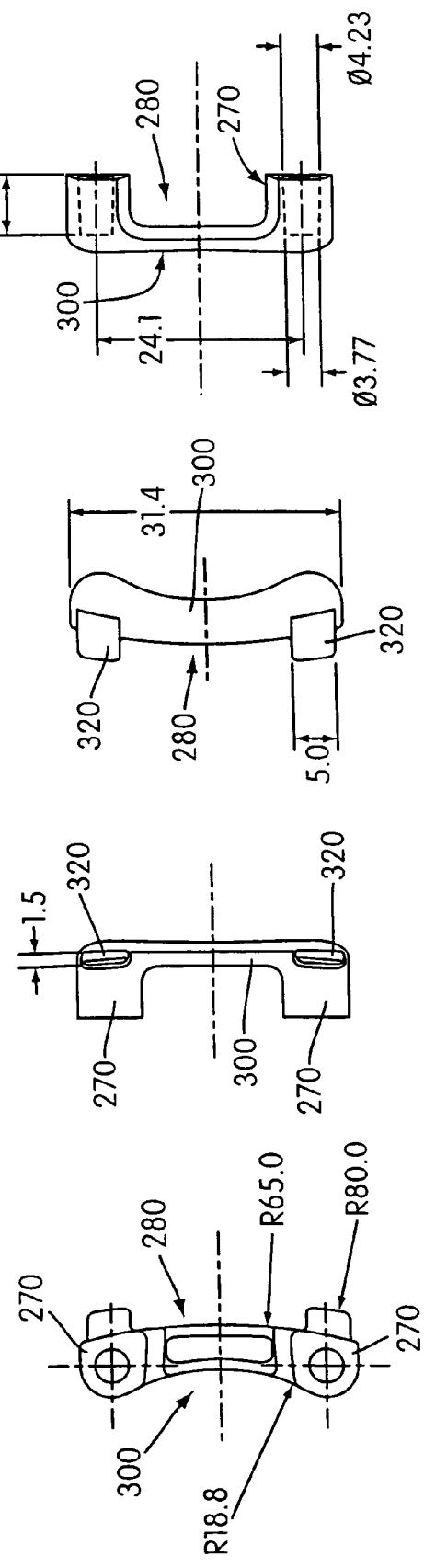
FIG. 4e
FIG. 4d
FIG. 4c ered breathing (SDB), and to mask ports for such masks.
MASK PORTS

CROSS REFERENCE TO RELATED APPLICATIONS

This is a continuation of U.S. application Ser. No. 10/162,234, filed Jun. 5, 2002, now allowed, which is a continuation of U.S. application Ser. No. 09/504,234, filed Feb. 15, 2000, now U.S. Pat. No. 6,439,230, which is a continuation-in-part of U.S. application Ser. No. 29/115,618, filed Dec. 16, 1999, now U.S. Design Pat. No. D443,355, which claims the benefit of Australian Application No. PQ 140, filed Jun. 18, 1999 and Australian Application No. 1916/99, filed Jun. 18, 1999, each incorporated herein by reference in its entirety.

FIELD OF THE INVENTION

The invention relates to masks suitable for the delivery of breathable gases to a patient for the treatment of sleep disordered breathing (SDB), and to mask ports for such masks.

BACKGROUND OF THE INVENTION

Respiratory masks used in the treatment of SDB may comprise a nasal mask, designed to fit over a patient's nose, or a full face mask designed to fit over the nose and mouth of the patient. In both cases, the mask is held in position by headgear.

The mask generally comprises a relatively rigid shell, termed a frame, which defines a rearwardly opening cavity covering the patient's nose and/or mouth and a soft portion, termed a cushion, which spaces the frame away from the face for comfortable contact.

The air or other breathable gas is supplied by a blower and passed along a flexible conduit to the mask. The conduit is typically of relatively large bore, for example approximately 2 cm diameter, with the mask frame having a gas inlet of comparable diameter.

In addition to the gas inlet, the mask may also have $CO_2$ washout vents and one or more small diameter ports through which supplemental oxygen may be introduced or measurements made. The ports typically comprise a pair of cylindrical connectors moulded into the mask frame, usually projecting forward from the front surface of the frame. The mask ports typically also include a cap which prevents leakage of air from the mask when the port is not in use.

Depending on the part construction and the relative diameters of the port and the tubing which supplies supplemental oxygen, the port may function as a male or a female connector.

The Mirage® nasal mask (ResMed Ltd.) is a generally triangular mask with a gas inlet tube extending upwards from its apex. The two ports of that mask are located in the front of the gas inlet tube just above the patient's eye level, between a pair of shield projections. A single cap of silicone rubber covers both ports, and has tabs at either end to facilitate removal by pulling on the tabs in a direction away from patient's face.

There is a need for ports which are conveniently located on the mask, which are protected from accidental breakage and which do not foul tubing. There is a need for a corresponding port cap which is sufficiently large so as to be easy to handle and which is not so small as to be easily lost.

SUMMARY OF THE INVENTION

The present invention provides a mask frame for a respiratory mask, said mask frame defining a mask cavity adapted for communication with a patient's airways and including a gas inlet adapted for connection to a supply of breathable gas, further including a recess in a lower portion of the mask frame, at least one mask port comprising a downwardly extending tubular spigot located in said recess, said spigot having a bore communicating with the mask cavity via a port aperture in the mask frame.

The cap is preferably constructed from a single piece of silicone or other elastomeric material with tabs preferably to the front of the mask when positioned on the ports. Preferably the base of the cap is flush with the base of the mask. Preferably, to remove the cap, the tabs are pulled in a downwards motion, relative to the front of the mask.

A further form of the invention provides a mask frame for a respiratory mask, said mask frame defining a mask cavity adapted for communication with a patient's airways including a gas inlet adapted for connection to a supply of breathable gas, further including at least one downwardly opening port located in a lower portion of the mask frame and communicating with the mask cavity.

BRIEF DESCRIPTION OF THE DRAWINGS

Further embodiments of the invention will now be described with reference to the accompanying drawings, in which:

FIG. 3b shows a section B-B from FIG. 3a.
FIG. 3c shows a section C-C from FIG. 3a.
FIG. 4a shows a perspective view of the port cap.
FIG. 4b shows an end view of the port cap.
FIG. 4c shows a top view of the port cap.
FIG. 4d shows a front view of the port cap.
FIG. 4e shows a bottom view of the port cap.
FIG. 4f shows a rear view of the port cap.
In FIGS. 4a to 4f approximate dimensions are indicated in mm.

DETAILED DESCRIPTION OF THE INVENTION

Figure 1:
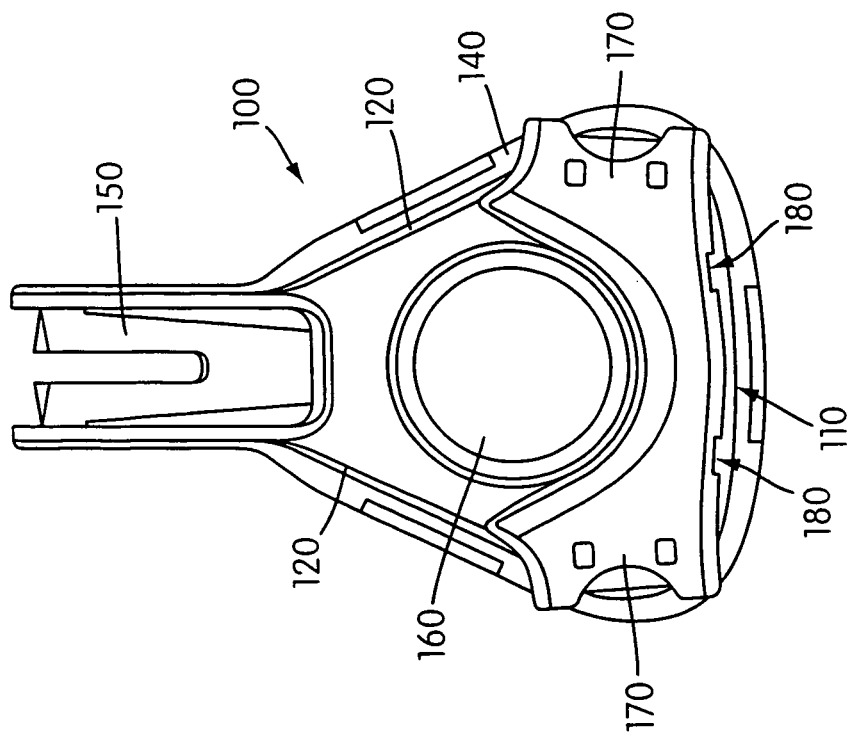
FIG. 1 shows a side perspective view of a mask frame.
Figure 2:
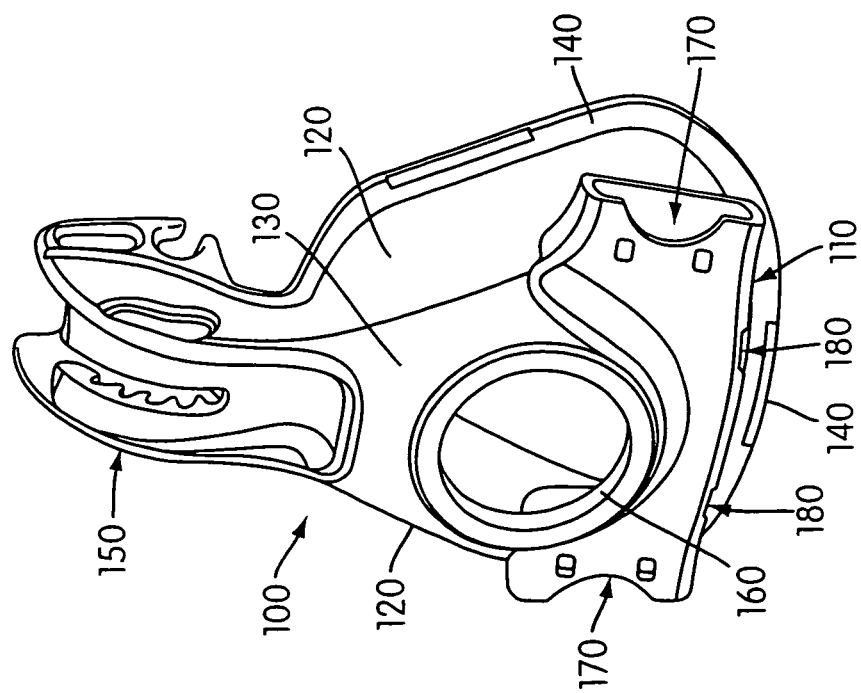
FIG. 2 shows a front view of the mask frame of FIG. 1.

FIGS. 1 and 2 illustrate a mask frame 100 for a nasal mask, formed as a moulded shell of polycarbonate or similar rigid material, which acts as a body onto which the other components of the mask are attached. A suitable material for the mask frame is Makrolon 2458 polycarbonate from Bayer.

The frame 100 is generally triangular in front view, having a base 110, a pair of inclined side walls 120 extending towards an apex and a front wall 130. The frame defines a mask cavity covering the patient's nose, and is open at its rear. A rim 140 at the rear edge of the base 110 and side walls 120 approximates the contours of the patient's face and is adapted for attachment of a soft mask cushion (not shown) to space the frame away from the patient's face for sealing and comfort. The apex of the frame has an extension 150 for attachment of a forehead support (not shown).

In the illustrated mask frame, a gas inlet aperture 160 is formed in the front wall 130, for connection of a gas supply conduit or similar, which may include an elbow connector (not shown) pivotably connected to the frame. In other forms of mask, the gas inlet aperture may be formed at the apex of the frame.

The mask frame further includes lower headgear connection points 170 for attachment to the headgear which holds the mask in place on the patient's face. Upper headgear connection points may be formed in the forehead support (not shown).

With reference to FIGS. 1 to 3a, it can be seen that the mask frame includes two ports 180, approximately 2.5 cm apart, located in recesses 190 in the base of the mask frame 100. These recesses are positioned in between the lower headgear strap connection points 170. The ports are positioned so that in use, oxygen or other breathable gas can be delivered close to the patient's nares.

Each port is formed as a tubular spigot 185 with an approximate external diameter of 4 mm and an approximate length of 1 cm. The spigot 185 forms the male connector onto which small bore tubing supplying, for example, oxygen, may be attached.

Figure 3A:
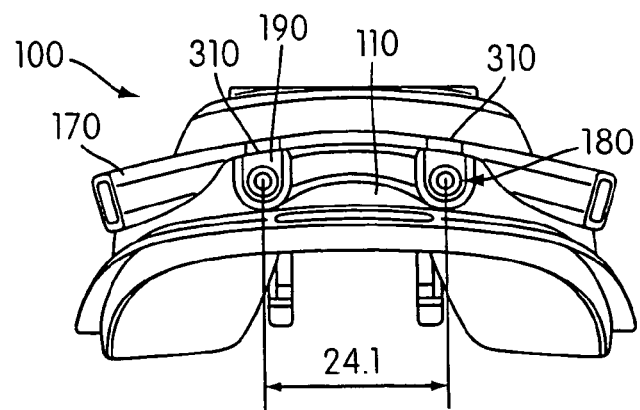
FIG. 3a shows a bottom view of the mask frame of FIG. 1.
Figure 3B:
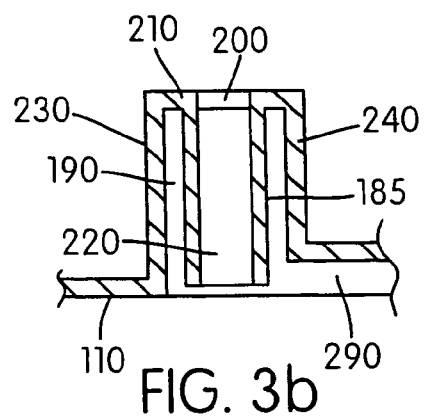
Figure 3C:
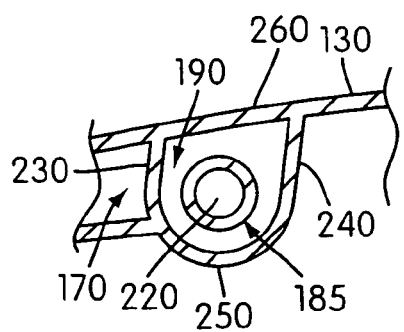

An elevational cross-section through the port is shown in FIG. 3b, and a lateral cross-section at FIG. 3c.

As best seen in FIGS. 3b and 3c, each recess 190 is approximately rectangular in elevation (FIG. 3a) and closed off from the mask cavity except for an aperture 200 extending through the recess upper wall 210 between the bore 220 of the spigot 185 and the mask cavity. The recess is bounded by the upper wall 210, side wall portions 230, 240 and a rear wall portion 250, and is open at its bottom end. A front wall 260 is formed as a continuation of the front wall 130 of the mask frame. The rear wall portion 250 and one or both side wall portions 230, 240 may be formed as a continuous curve.

These boundary walls 230, 240, 250, 260 of the recess are spaced from the spigot by a sufficient distance, for example at least 1 mm, to allow a small bore oxygen tube to be pushed onto the spigot, and also to allow the closure portion 270 of a cap 280 (FIGS. 4a to 4f) to be retained.

The base 110 of the mask also includes a shallow bridging recess 290 for receiving the bridge piece 300 joining the two closures 270 of the cap 280.

The bottom edge of the frame front wall 130 includes a pair of small notches 310 through which gripping tabs 320 of the cap extend, so that the tabs extend forward of the front wall for gripping by the user. Pulling downwards on the tab will remove the respective closures 270 from its spigot 185 to allow attachment of an oxygen tube or a tube leading to a measurement device.

The cap 280 is suitably formed of a relatively soft elastomeric material, such as Dow Silastic 94-595 HC silicone.

As can be seen in FIGS. 1 and 2, the above construction results in the bottom of the cap 280 being substantially flush with the base 110 of the frame 100, providing a compact and aesthetically pleasing arrangement.

The asymmetric shape of the recessed chamber and corresponding shape of the cap 280 reduces the likelihood that the cap 280 will be incorrectly positioned back-to-front.

A further advantage of recessing the ports into the mask frame is that the dead volume of the frame is reduced. A further advantage of providing access from the bottom of the mask frame is that the likelihood of fouling the gas delivery conduit is reduced where a swivel connection is used to provide air from the flow generator.

Another advantage is that the loss of supplemental oxygen through the vent is reduced by positioning the port away from the main vent path.

In other embodiments, there may be one port, or there may be more than two ports. Furthermore, ports may have individual caps. Ports may be connected by way of a small bore tubing or in any other suitable manner to a manometer for measuring pressure in the mask cavity during the setting up of the device or during treatment of SDB. Alternatively, one or more ports may be used in conjunction with transducers and control algorithms to control the operation of an automatically adjusting device.

In an alternative embodiment, a larger diameter cylinder is used for the port, hence the cylinder will function as a female connector with respect to the supplemental oxygen tubing.

In another embodiment, the spigots could extend within the mask frame to bring the oxygen supply closer to the nares.

Figure 5A:
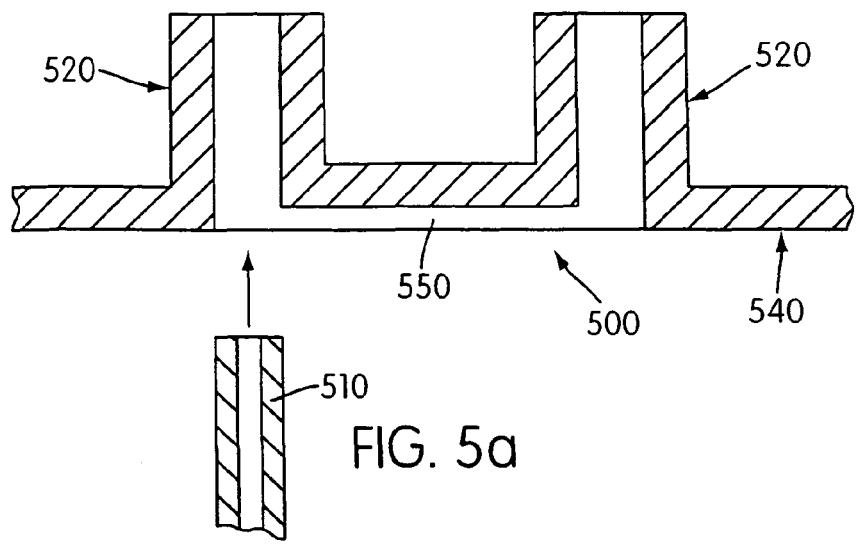
FIGS. 5a to 5c schematically illustrate an alternative embodiment of the invention.
Figure 5B:
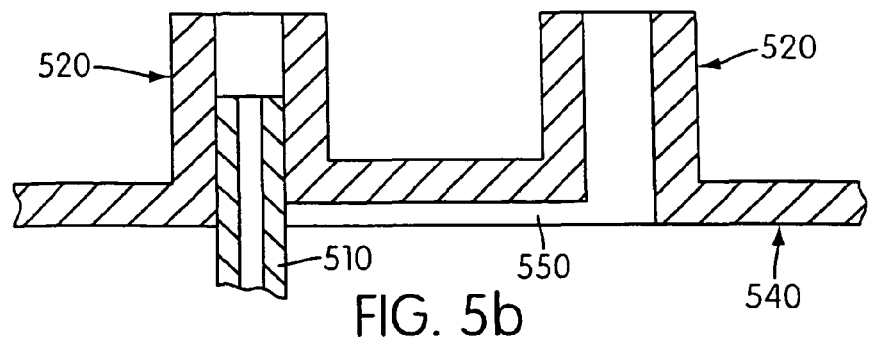
Figure 5C:
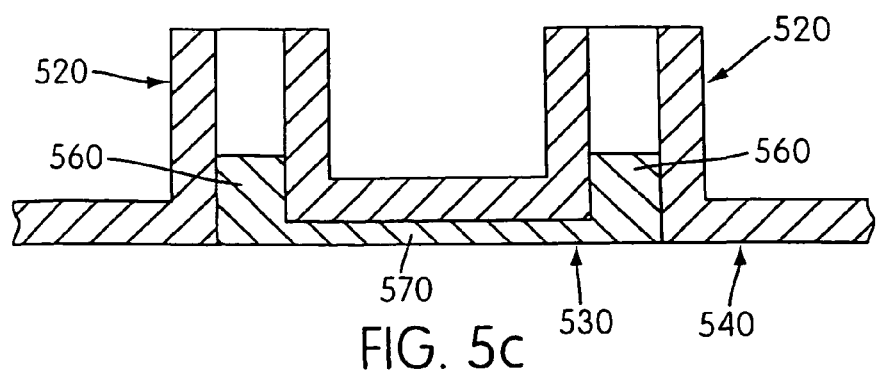

FIGS. 5a to 5c are schematic front elevational cross-sections of an alternative mask port arrangement 500 with, respectively, an oxygen delivery tube 510 being inserted into a port 520 (FIG. 5a), the delivery tube in position in the port (FIG. 5b), and the tube removed and a cap 530 inserted (FIG. 5c).

The position and orientation of the ports 520 is generally similar to that described above with reference to FIGS. 1 to 3c except that the ports 520 are formed as tubes extending upwards into the mask cavity, and open at their upper ends. In common with the previously described embodiment, the base 540 of the mask frame includes a pair of these recessed mask ports, joined by a shallow bridging recess 550.

As can be seen from FIGS. 5a and 5b, the port 520 acts as a female connector for insertion from below of a corresponding oxygen supply tube 510 having a diameter chosen for substantially sealing engagement in the port.

As shown in FIG. 5c, the configuration of the cap 530 is generally similar to that of FIGS. 4a to 4f, including a pair of closure portions 560 joined by a bridging portion 570, except that the closure portions for sealing the ports when not in use are preferably formed as solid plugs rather than as cup-shaped closures as in FIGS. 4a to 4f.

In another embodiment, the tabs 320 of the cap 280 are below the mask, rather than in front.

Although the invention has been described with reference to particular embodiments, it is to be understood that these embodiments are merely illustrative of the application of the principles of the invention. Numerous modifications may be made in the illustrative embodiments of the invention and other arrangements may be devised without departing from the spirit and scope of the invention.

The invention claimed is:

1. A mask frame for a respiratory mask, the mask frame having a wall defining a mask cavity adapted for communication with a patient's airways and including a gas inlet oriented in a first plane and adapted for connection to a supply of breathable gas, further including at least one port formed in a lowermost portion of the mask frame, wherein the at least one port is defined by portions of the wall that form a substantially cylindrical bore, wherein the at least one port communicates with the mask cavity via a port aperture, wherein the port is oriented in a second plane substantially perpendicular to the first plane, and wherein the substantially cylindrical bore of the at least one port extends from the lower portion inside the mask cavity.

2. A mask frame according to claim 1, further comprising at least one headgear attachment point.

3. A mask frame for a respiratory mask, the mask frame having a wall defining a mask cavity adapted for communication with a patient's airways and including a gas inlet oriented in a first plane and adapted for connection to a supply of breathable gas, further including at least one port formed in a lowermost portion of the mask frame, wherein the at least one port is defined by portions of the wall that form a substantially cylindrical bore, wherein the at least one port communicates with the mask cavity via a port aperture, and wherein the port is oriented in a second plane substantially perpendicular to the first plane, the mask frame having a front wall, a base wall, an apex opposite the base wall, and a pair of inclined side walls extending from respective opposed ends of the base wall to the apex, wherein the at least one port is formed in the base wall.

4. A mask frame according to claim 3, wherein the cylindrical bore includes a first axis that is adapted to receive a cylindrical tube having a second axis, the first and second axes being coincident when the cylindrical tube is pushed into direct engagement with a wall of the cylindrical bore.

5. A mask frame for a respiratory mask, the mask frame having a wall defining a mask cavity adapted for communication with a patient's airways and including a gas inlet oriented in a first plane and adapted for connection to a supply of breathable gas, further including at least one port formed in a lowermost portion of the mask frame, wherein the at least one port is defined by portions of the wall that form a substantially cylindrical bore, wherein the at least one port communicates with the mask cavity via a port aperture, wherein the port is oriented in a second plane substantially perpendicular to the first plane, and wherein the at least one port is formed within a recess including an upper wall portion, opposed side wall portions and a rear wall portion, so as to allow a tube to be pushed through an open bottom end of the at least one recess.

6. A mask frame according to claim 5, wherein a front wall of the at least one recess is formed by part of a front wall of the mask frame.

7. A mask frame according to claim 5, wherein the opposed side wall portions of the at least one recess and the rear wall portion of the at least one recess are formed as one substantially continuous curved wall.

8. A mask frame according to claim 5, wherein the opposed side wall portions of the at least one recess, the rear wall portion of the at least one recess, and a front wall portion of the at least one recess are formed as one substantially continuous curved wall in the form of a tube.

9. A mask frame according to claim 5, wherein the recess aperture extends through the upper wall portion of the at least one recess.

10. A mask frame according to claim 5, wherein the gas inlet is located in the front wall of the mask frame, above the at least one recess.

11. A mask frame for a respiratory mask, the mask frame having a wall defining a mask cavity adapted for communication with a patient's airways and including a gas inlet adapted for connection to a supply of breathable gas, further including at least one port formed in a lowermost portion of the mask frame, wherein the at least one port is defined by portions of the wall that form a substantially cylindrical bore, wherein the at least one port communicates with the mask cavity via a port aperture, wherein the at least one port is formed within a recess including an upper wall portion, opposed side wall portions and a rear wall portion, so as to allow a tube to be pushed through an open bottom end of the at least one recess, wherein the at least one port is formed within a recess including an upper wall portion, opposed side wall portions and a rear wall portion, so as to allow a tube to be pushed through an open bottom end of the at least one recess, and wherein the upper wall portion of the recess defines a tube stop formed from a portion of the mask frame.

12. A mask flame for a respiratory mask, the mask flame having a wall defining a mask cavity adapted for communication with a patient's airways and including a gas inlet oriented in a first plane and adapted for connection to a supply of breathable gas, further including at least one port formed in a lower portion of the mask frame, wherein the at least one port is defined by portions of the wall that form a substantially cylindrical bore, wherein the at least one port communicates with the mask cavity via a port aperture, wherein the port is oriented in a second plane substantially perpendicular to the first plane; wherein the substantially cylindrical bore of the at least one port extends from the lower portion inside the mask cavity and wherein the frame further comprises a pivotable elbow provided to the gas inlet.

13. A mask frame according to claim 12, further comprising at least one headgear attachment point.

14. A mask frame for a nasal respiratory mask, the mask frame defining a mask cavity adapted for communication with a patient's airways, the mask frame comprising:
  a front wall, a base and an apex;
  a pair of inclined side walls extending from respective opposed ends of the base to the apex;
  a pair of lower headgear connection points provided to the mask frame;
  a pair of recesses formed between the pair of lower headgear connection points in the base, the pair of recesses each extending inward towards the mask cavity and being bounded by at least one upper wall portion, opposed side wall portions, a rear wall portion and a front wall portion formed as part of the front wall of the mask frame, and being open at a bottom end thereof;
  a pair of mask ports, each mask port comprising a downwardly extending tubular spigot located at least partly within a respective one of the recesses, each spigot including a bore communicating with the mask cavity via a port aperture extending through the upper wall portion of each recess;
  a gas inlet for connection to a supply of breathable gas, the gas inlet being located in the front wall of the mask frame and above the recesses; and
  a removable port cap having a pair of closure portions, each closure portion adapted to be pushed into a respective recess to cover the mask port, the port cap including a bridge portion joining the pair of closure portions, each closure portion having a gripping tab which extends in use forward of the front wall of the mask frame, wherein the recesses and the port cap are shaped so that the port cap only fits in the recesses in a single orientation.

15. A mask frame according to claim 14, wherein the mask ports are separated by approximately 2.5 cm.

16. A mask frame according to claim 15, wherein the mask ports are positioned to deliver gas close to the nares of a patient.

17. A mask frame according to claim 16, wherein the port cap is formed of an elastomeric material.

18. A mask frame according to claim 17, wherein the material is silicone.

19. A mask frame according to claim 18, wherein the tubular spigot has an external diameter of approximately 4 mm.

20. A mask frame according to claim 19, wherein the tubular spigot has a length of approximately 1 cm.

21. A mask frame according to claim 20, wherein the opposed side wall portions, the rear wall portion, and the front wall portion of each of the recesses are spaced apart from the tubular spigot by at least 1 mm.

22. A mask frame according to claim 21, further comprising a pair of notches formed in the front wall of the mask frame, wherein the gripping tab of a respective one of the closure portions extends through the notches.

23. A mask frame according to claim 22, wherein a base of the port cap is substantially flush with the base of the mask frame in use.

24. A mask frame according to claim 23, further comprising an extension connected to the apex of the frame, and a forehead support connected to the extension.

25. A mask frame according to claim 24, wherein the mask frame is polycarbonate.

26. A mask for treatment of sleep disordered breathing, comprising:
- the mask frame of claim 14;
- a mask cushion connected to the frame, the mask cushion for sealing the mask with a face of the patient;
- headgear connected to the lower headgear connection points; and
- an elbow connected between the gas inlet and the supply of breathable gas.

27. A mask according to claim 26, further comprising an extension connected to the apex of the frame, and a forehead support connected to the extension.

28. A mask according to claim 27, wherein the forehead support includes upper headgear connection points connected to the headgear.

* * * * *